(12) United States Patent
Li

(10) Patent No.: US 8,314,110 B2
(45) Date of Patent: Nov. 20, 2012

(54) COMPOUNDS FOR TREATING MENTAL DISORDERS, AND PREPARATION AND USES THEREOF

(76) Inventor: Youxin Li, Zhuzhou (CN)

( * ) Notice: Subject to any disclaimer, the term of this patent is extended or adjusted under 35 U.S.C. 154(b) by 405 days.

(21) Appl. No.: 12/596,516

(22) PCT Filed: Apr. 18, 2008

(86) PCT No.: PCT/CN2008/000803
§ 371 (c)(1),
(2), (4) Date: Jan. 13, 2010

(87) PCT Pub. No.: WO2008/128436
PCT Pub. Date: Oct. 30, 2008

(65) Prior Publication Data
US 2010/0113482 A1 May 6, 2010

(30) Foreign Application Priority Data
Apr. 19, 2007 (CN) .......................... 2007 1 0098304

(51) Int. Cl.
*A01N 43/90* (2006.01)
*A61K 31/519* (2006.01)
*C07D 239/70* (2006.01)

(52) U.S. Cl. ................................. 514/259.41

(58) Field of Classification Search ............. 514/259.41; 544/282
See application file for complete search history.

(56) References Cited

U.S. PATENT DOCUMENTS
5,158,952 A 10/1992 Janssen et al.

FOREIGN PATENT DOCUMENTS
| CN | 1093762 | 11/2002 |
| CN | 1160074 | 8/2004 |
| WO | WO 97/44039 | * 5/1997 |

OTHER PUBLICATIONS

Youdim, The Path from Anti Parkinson Drug Selegiline and Rasagiline to Multifunctional Neuroprotective Anti Alzheimer Drugs Ladostigil and M30, Current Alzheimer Research, 3, 541-550 (2006).*

* cited by examiner

*Primary Examiner* — Erich A Leeser
(74) *Attorney, Agent, or Firm* — The Webb Law Firm

(57) ABSTRACT

The present invention relates to a compound of formula (I), an optical isomer or a pharmaceutically acceptable salt thereof, its preparation and uses, wherein R is defined as herein. Such compounds can be presented as an optical isomer or a racemic mixture. The compounds can be metabolized in vivo to form a pharmacologically active substance as antagonist of neurotransmitters, and can be used for the treatment of the related mental disorders such as schizophrenia.

16 Claims, 2 Drawing Sheets

COMPOUNDS FOR TREATING MENTAL DISORDERS, AND PREPARATION AND USES THEREOF

TECHNICAL FIELD OF THE INVENTION

The present invention relates to a compound of formula (I) and salts thereof, a process for preparing the same, a pharmaceutical composition comprising the same, and their use for the treatment or auxiliary treatment of mental disorders.

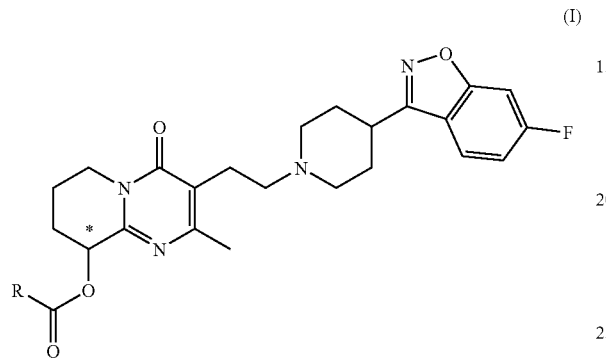

BACKGROUND OF THE INVENTION

It has been reported that the compound [formula (II)] [3-{2-[4-(6-fluoro-benzo[d]isoxazol-3-yl)piperidin-1-yl]-ethyl}-9-hydroxy-2-methyl-6,7,8,9-tetrahydro-pyrido[1,2-a]pyrimidin-4-one; or IUPAC name: 3-{2-[4-(6-fluorobenzo[d]isoxazol-3-yl)-1-piperidyl]ethyl}-7-hydroxy-4-methyl-1,5-diazabicyclo[4.4.0]deca-3,5-dien-2-one; CAS Nr. 144598-75-4; MW 426.48; Paliperidone or 9-OH risperidone or 9-hydroxy risperidone] is a benzoisoxazole derivative and one of new generation antipsychotics. The compound [formula (II)] is a selective monoaminergic antagonist having unique properties, and has a high affinity to serotoninergic 5-HT2 receptor and dopamine D2 receptor. The compound [formula (II)] can also binds to α1-adrenergic receptor, and binds to histaminergic H1 receptor and α2-adrenoceptor with a relatively low affinity. The compound [formula (II)] does not bind to a cholinergic receptor. The compound [formula (II)] is a potent D2 antagonist and can improve positive symptoms of schizophrenia, but it may cause less motor function inhibition and catalepsy than classic antipsychotics. Its balanced antagonistic effects on serotonin and dopamine of central nervous system may reduce the possibility of occurrence of extra pyramidal side effects, and its therapeutic effects may be extended to negative symptoms and emotional symptoms of schizophrenia.

The compound [formula (II)] is a new generation of psychotropic relative to Risperidone. U.S. Food and Drug Administration approved the marketing of an oral sustained release formulation of the compound [formula (II)] (Invega) developed by JANSSEN Pharmaceuticals, Inc in December 2006 for the treatment of mental disorders. Since the hydroxyl group of the compound results in an increased hydrophilicity, the absorption rate via oral administration is reduced, and the absolute bioavailability of the compound is only 28%, which is far lower than that of Risperidone (at least 70%), so that the daily dosage of the compound increased significantly, which in turn lead to increase in the pre-system side effects of the possible unabsorbed drug. The long-chain fatty acid ester of the compound [formula (II)] was reported in WO99/25354, but it is metabolized very slowly to form the compound [formula (II)] in vivo and cannot rapidly achieve the effective therapeutic effects. In order to overcome the above drawbacks associated with the compound [formula (II)] and fatty acid esters thereof, a series of derivatives of the compound [formula (II)] (the compounds of formula (I)) were synthesized, used as prodrugs of the compound [formula (II)] and reduced by rapid metabolism in vivo to form the compound [formula (II)] upon being taken, thereby achieving therapeutic effects.

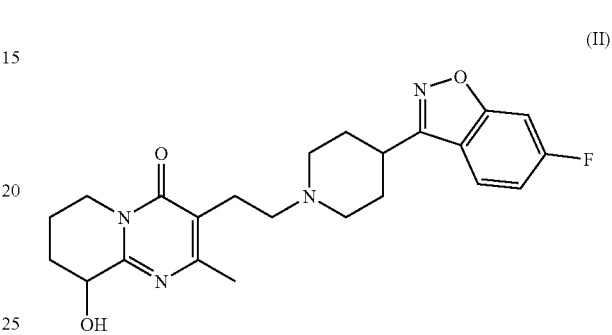

CONTENTS OF THE INVENTION

The object of the present invention is to develop a new compound, which is a prodrug for the treatment of mental disorders. The below compounds of formula (I) obtained thus by the inventors have an advantage of being rapidly metabolized in vivo to form the compound [formula (II)], thereby having an increased bioavailability and reduced pre-system side effects caused by the possible unabsorbed drug, facilitating the regulation of dosage and therapeutic effects, reducing side effects and the risk of interaction with other drugs.

The present invention relates to a compound represented by formula (I), an optical isomer or a pharmaceutically acceptable salt thereof, which is a prodrug for the treatment of mental disorders,

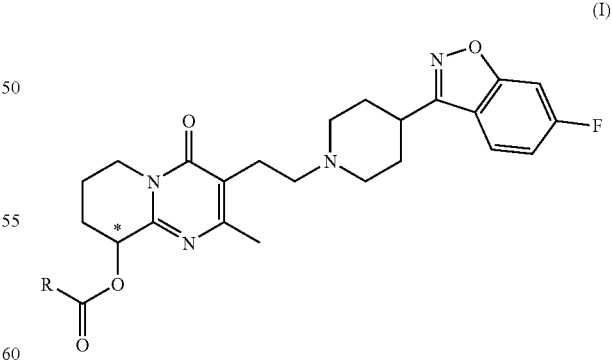

wherein, the chiral center (*) can be R or S or RS (racemic mixture);

R is an aryl having 7-20 carbon atoms; or a saturated alkoxy having 1-20 carbon atoms or an unsaturated alkoxy having 2-20 carbon atoms or a cycloalkoxy having 4-20 carbon atoms or an arylalkoxy having 7-20 carbon atoms; or an amino of the following formula having 1-20 carbon atoms:

wherein R2 and R3 independently are hydrogen, a saturated alkyl having 1-10 carbon atoms or a non-saturated alkyl having 2-10 carbon atoms or an aryl having 7-10 carbon atoms.

R is an aryl having 7-20 carbon atoms, preferably, but not limited to:

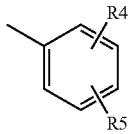

wherein, R4 and R5 independently are hydrogen, a saturated alkyl or alkoxy having 1-6 carbon atoms, an unsaturated alkyl or alkoxy having 2-6 carbon atoms, OH, Cl, F, CN, carboxyl and ester group; preferably but not limited to hydrogen, methyl, ethyl, methoxy, ethoxy, fluorine or carboxyl.

R is a saturated alkoxy having 1-20 carbon atoms or an unsaturated alkoxy having 2-20 carbon atoms or a cycloalkoxy having 4-20 carbon atoms, preferably but not limited to methoxy, ethoxy, propoxy, isopropoxy, butoxy, isobutoxy, tert-butoxy, pentoxy, cyclohexyloxy; or an arylalkoxy having 7-20 carbon atoms, preferably but not limited to:

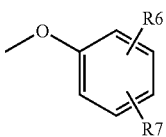

wherein, R6 and R7 independently are hydrogen, a saturated alkyl or alkoxy having 1-6 carbon atoms, an unsaturated alkyl or alkoxy having 2-6 carbon atoms, OH, Cl, F, CN, carboxyl and ester group; preferably but not limited to hydrogen, methyl, ethyl, methoxy, ethoxy, fluorine or carboxyl.

R is an amino of the following formula having 1-20 carbon atoms:

wherein R2 and R3 independently are hydrogen, a saturated alkyl having 1-10 carbon atoms or a non-saturated alkyl having 2-10 carbon atoms, preferably but not limited to methyl, ethyl, propyl, isopropyl, butyl, isobutyl, tert-butyl; or an aryl having 7-10 carbon atoms, preferably but not limited to:

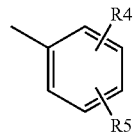

wherein, R4, R5 independently are hydrogen, a saturated alkyl or alkoxy having 1-6 carbon atoms, an unsaturated alkyl or alkoxy having 2-6 carbon atoms, OH, Cl, F, CN, carboxyl and ester group; preferably but not limited to hydrogen, methyl, ethyl, methoxy, ethoxy, fluorine or carboxyl.

According to the present invention, the term "optical isomer" represents an R- or S-optical isomer or an RS-racemic mixture of a compound of formula (I) or a pharmaceutically acceptable salt thereof.

According to the present invention, the representative compounds of formula (I) include:

3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl benzoate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-methylbenzoate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 3-methylbenzoate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-methylbenzoate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-methoxybenzoate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 3-methoxybenzoate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-methoxybenzoate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-fluorobenzoate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 3-fluorobenzoate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-fluorobenzoate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-carboxybenzoate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl methyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl ethyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl propyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl isopropyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl butyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl isobutyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl tert-butyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-methylbutyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl n-pentyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-pentyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 3-pentyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl isopentyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl neopentyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl hexyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl cyclohexyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl phenyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-methylphenyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 3-methylphenyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-methylphenyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-methoxyphenyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 3-methoxyphenyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-methoxyphenyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-fluorophenyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 3-fluorophenyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-fluorophenyl carbonate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl N,N-dimethylcarbamate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl N,N-diethylcarbamate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl N,N-dipropylcarbamate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl N,N-diisopropylcarbamate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl N,N-dibutylcarbamate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl N,N-diisobutylcarbamate 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl N,N-di-tert-butyl-carbamate and various salts and optical isomers thereof.

According to the conventional methods for preparing pharmaceutical formulations in the art, the compound of formula (I) of the present invention, including optical isomers and racemic mixtures and pharmaceutically acceptable salts thereof, can be formulated into suitable dosage forms for oral, injection, transdermal, intranasal, mucosal administration and by inhalation and the like. The dosage forms suitable for oral administration can be either solid tablets, capsules, soft capsules or drop pills, or solutions, suspensions, emulsions or powders, and can be conventional dosage forms, sustained release dosage forms, site specific delivery dosage forms, fast release dosage forms or orally disintegrating dosage forms. The injection administration can be intravenous injection, hypodermical injection, intramuscular injection or intraperitoneal injection, and the suitable dosage forms therefore can be either solutions, suspensions or emulsions, or conventional or long acting dosage forms such as implants, microspheres or gels. The dosage forms suitable for transdermal administration can be transdermal patches, gels or other dosage forms for transdermal administration. The dosage forms suitable for nasal administration and by inhalation can be solutions, suspensions, emulsions or powders. The dosage forms suitable for mucosal administration can be solutions, suspensions, emulsions, powders or suppositories.

The present invention further relates to a pharmaceutical composition comprising an effective amount of a compound of formula (I) and a compatible and pharmaceutically acceptable carrier or diluent. The carrier can be any inert organic or inorganic substances, such as water, gelatin, cellulose, starch, biodegradable polymeric adjuvants such as polyesters or polycarbonates or copolymers of any two or three components thereof, other pharmaceutically active substances, as well as conventional additives such as stabilizers, wetting agents, emulsifiers, flavoring agents and buffers.

The compound of formula (I) of the present invention, including optical isomers, racemic mixtures and pharmaceutically acceptable salts thereof, as antagonists of neurotransmitters, can be used for the treatment of mental disorders such as schizophrenia, and the daily dosage thereof can be 0.01-100 mg which can be administrated by single or multiple doses.

Figure 1A:
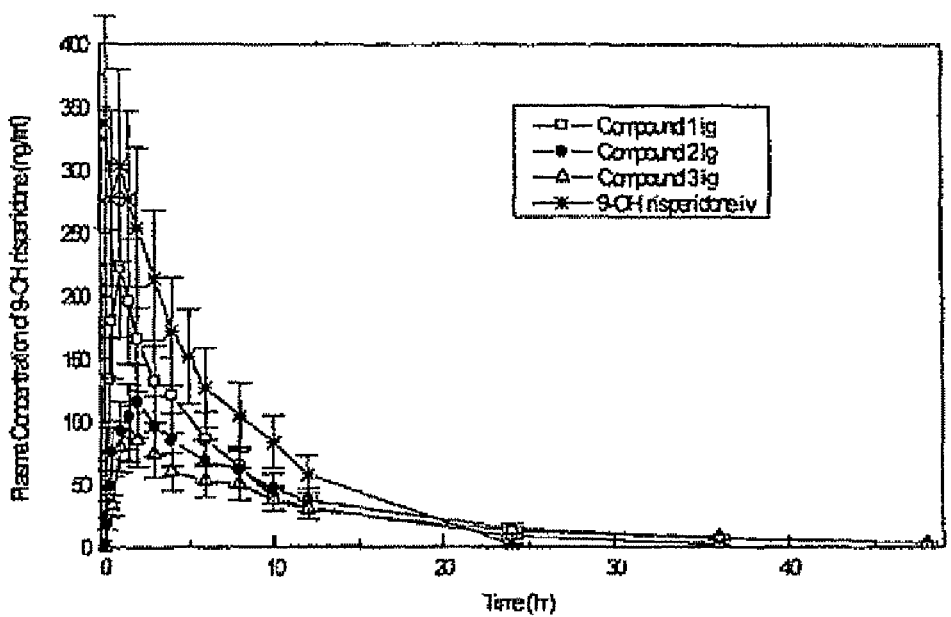
FIG. 1 shows the absorption and metabolism of the compound [formula (II)] and its prodrugs—compounds 1, 2, 3, 5, 6, 7 and compound 8 in Beagles.

A. concentration changes of the active metabolite compound of formula (II) the compounds 1, 2 and 3 (ig) and the compound [formula (II)] (iv) in blood;

B. concentration changes of the active metabolite compound of formula (II) of the compounds 5, 6, 7 and 8 (ig) and the compound [formula (II)] (iv) in blood;

C. measurements of the concentrations of prototype compounds 1, 2, 3, 5, 6, 7 and 8 for the compounds 1, 2, 3, 5, 6, 7 and 8 (ig) in blood.

CONCRETE MODELS FOR CARRYING OUT THE INVENTION

The present invention is further illustrated by the following examples, without being construed to restrict the scope of the invention in any way.

A. Synthesis of the Compound [Formula (II)]

1. Preparation of 3-(2-chloroethyl)-2-methyl-9-benzyloxy-6,7,8,9-tetrahydropyrido[1,2-a]pyrimidin-4-one Toluene 1500 ml, 2-amino-3-benzyloxy-pyridine 120 g (0.65 mole), 2-acetyl y-butyrolactone 114 ml (1.05 mole) were added to a reaction bottle, and phosphorus oxychloride 300 ml (3.21 mole) was added dropwise. The reaction was conducted at 90-93° C. for 5 hours. The solvent was distilled out at a reduced pressure, the residue was poured into brash ice, adjusted to a pH 9 with 25% ammonia, extracted with chloroform for three times (100 ml per time), washed with water, dried over anhydrous magnesium sulfate. The solvent was distilled out at a reduced pressure, the residue while hot was dissolved in 100 ml isopropanol, and stood overnight. The precipitated crystal was filtered out, washed with isopropanol, and dried to obtain 65.0 g of light pink crystal (yield 31%). Mp: 139.9-140.9° C.

2. Preparation of 3-(2-chloroethyl)-2-methyl-9-hydroxy-6,7,8,9-tetrahydro-pyrido[1,2-a]pyrimidin-4-one At room temperature, 3-(2-chloroethyl)-2-methyl-9-benzyloxy-6,7,8,9-tetrahydro-pyrido[1,2-a]pyrimidin-4-one 4.0 g (0.0122 mole) was charged into a 250 mL three-necked bottle, 80 mL methanol was added, and then concentrated hydrochloric acid (about 25 drops) was added dropwise with stirring to adjust pH to 3.0. After the dissolution was completed, 1.8 g of wet 5% Pd—C (water content: 56%) (W/W: 10/1) was added, argon gas was fed to exchange atmosphere for three times, hydrogen gas was fed to exchange atmosphere for three times, the reaction was conducted at 27° C. for about 36 hours, and TLC (ethyl ether:n-hexane:methanol:triethylamine=2 mL:0.5 mL:6 drops:6 drops) was used to detect the debenzylated product. The reaction was stopped after all starting materials were consumed.

A light green liquid was obtained by sucking filtration, and distilled at a reduced pressure to remove solvent to obtain a dark green viscous liquid. About 16 mL distilled water was added, dissolution was conducted under ultrasound, the temperature was decreased to 5° C. by using an icewater bath, and the pH was adjusted to 10-11 by adding 2N aqueous sodium hydroxide so as to precipitate a large amount of white solid when the pH was close to its end. The white solid was filtered out at a reduced pressure. The filtrate was extracted with 2×20 mL of dichloromethane. The organic layers were combined and washed with saturated aqueous NaCl solution for twice (10 mL per time), dried over anhydrous magnesium sulfate. Light yellow solids were obtained after the solvent was distilled out. The resulting solids were combined and dried to obtain 2.14 g product (yield: 72.6%). Mp: 100.8-102.7° C.

3. Preparation of 3-{2-[4-(6-fluoro-1,2-benzoisoxazol-3-yl)-1-piperidinyl]-ethyl}-2-methyl-9-hydroxy-6,7,8,9-tetrahydropyrido[1,2-a]pyrimidin-4-one (the compound [formula (II)])

Methanol 100 ml, 6-fluoro-3-piperidin-4-yl-1,2-benzoisoxazole hydrochloride 10.27 g (0.04 mole), 3-(2-chloroethyl)-2-methyl-9-benzyloxy-6,7,8,9-tetrahydro-pyrido[1,2-a]pyrimidin-4-one 9.17 g (0.04 mole), diisopropylamine 10 ml were added to a reaction bottle and reacted at 60° C. for 14 hours. The solvent was distilled out at a reduced pressure, water and chloroform (q.s.) were added, the pH was adjusted to 8 with 10% NaOH, the obtained chloroform extract was washed with water for three times, and dried over anhydrous magnesium sulfate. The solvent was distilled out at a reduced pressure to obtain a viscous product at which time 100 mL isopropanol was added to make it dissolve, and stood overnight. The precipitated crystal was filtered out to obtain a crude product 9.0 g.

Column chromatography refinement: a column chromatography on silica gel using chloroform-methanol (100:2) as eluant was conducted to obtain the refined product, the compound [formula (II)] 5.6 g (yield: 32.8%), mp: 174.7-178.3° C.

B. Synthesis of Aromatic Carboxylic Acid Esters of the Compound [Formula (II)]

General Methods and Processes

Reaction scheme:

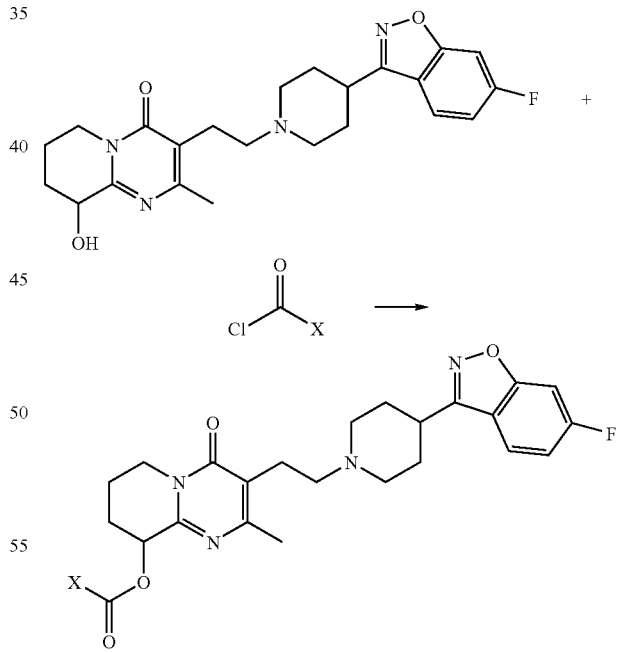

wherein X is an aryl having 7-20 carbon atoms, such as phenyl, tolyl, methoxyphenyl, etc.

To 10 mL anhydrous pyridine, the compound [formula (II)] 0.43 g (1 mmol) was added, dissolved under stirring at room temperature, an aromatic acid chloride (2 mmol) was added dropwise, and the reaction is conducted until starting materials spots disappeared on TLC. The reaction was poured into water, adjusted to a pH of 9 with 10% aqueous NaOH, and extracted with chloroform for three times (15 mL per time). The extract was washed with water, and dried over anhydrous magnesium sulfate. The solvent was distilled out at a reduced pressure to obtain a product. The product was dissolved in 2 mL anhydrous ethanol, and 3 mL of saturated anhydrous ethanol-HCl solution was added dropwise, and the mixture was standed overnight. The precipitated solid was filtered out, washed with ethyl acetate, dried to obtain 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl aromatic carboxylate hydrochloride.

The following compounds were synthesized and characterized according to the above reaction scheme.

EXAMPLE 1

Synthesis of Aromatic Carboxylic Acid Esters [Formula (II)] of the Compound [Formula (II)]

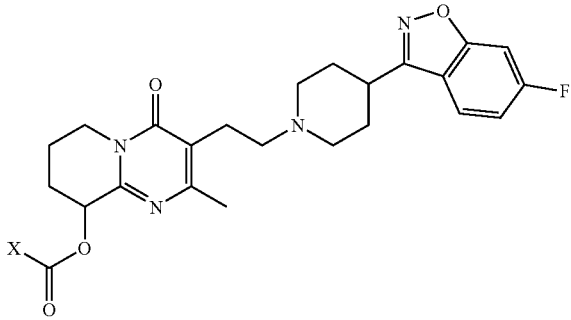

(III)

3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl benzoate is given below as example.

To 10 mL anhydrous pyridine, the compound [formula (II)] 0.43 g (1 mmol) was added, dissolved under stirring at room temperature, benzoyl chloride 0.28 g (2 mmol) was added dropwise, and the reaction was conducted until starting materials spots disappeared on TLC. The reaction was poured into water, adjusted to a pH of 9 with 10% NaOH, and extracted with chloroform for three times (15 mL per time). The extract was washed with water, and dried over anhydrous magnesium sulfate. The solvent was distilled out to obtain a product. The product was dissolved in 2 mL anhydrous ethanol, 3 mL of saturated anhydrous ethanol-HCl solution was added dropwise, and the mixture was standed overnight. The precipitated solid was filtered out, washed with ethyl acetate, dried to obtain 3-{2-[4-(6-fluoro-1,2-benzoisoxazol-3-yl)-1-piperidinyl]-ethyl}-2-methyl-4-oxo-6,7,8,9-tetrahydro-pyrido[1,2-α]pyrimidin-9-yl benzoate dihydrochloride 0.33 g. The product was converted to obtain 3-{2-[4-(6-fluoro-1,2-benzoisoxazol-3-yl)-piperidin-1-yl]ethyl}-2-methyl-4-oxo-6,7,8,9-tetrahydro-pyrido[1,2-α]pyrimidin-9-yl benzoate 0.30 g. Melting point is 138.6-140.7° C.

The following compounds were synthesized and characterized according to this method.

Compound 1. 3-{2-[4-(6-fluoro-1,2-benzoisoxazol-3-yl)-1-piperidinyl]-ethyl}-2-methyl-4-oxo-6,7,8,9-tetrahydro-pyrido[1,2-α]pyrimidin-9-yl benzoate $^1$H-NMR(CDCl$_3$):2.10-2.27(8H,m,—CH$_2$—), 2.29(3H, s,—CH$_3$), 2.58, 2.78, 3.18(6H,t,t,t,>N—CH$_2$—), 3.91, 4.11 (2H,m,m,—CON—CH$_2$—), 3.10(1H,m,

≧—CH—), 6.02(1H,t,≧—CH—O—), 7.02-8.06 (8H,m, Ar—H).

$^{13}$C-NMR: 20.61, 22.90, 23.79, 27.69(2C), 33.66, 34.27, 42.65, 48.73(2C), 50.74, 79.57, 99.70, 107.36, 114.31, 118.63, 126.83, 129.07(2C), 130.09(2C), 130.97, 133.02, 141.91, 143.75, 155.11, 157.00, 163.78, 165.58, 166.57.

Compound 2. 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-methyl-benzoate The reaction conditions were substantively the same, except that benzoylchloride was replaced with 4-methylbenzoylchloride to obtain 0.36 g of 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-methylbenzoate.

Mp: 112.1-113.5° C.

$^1$H-NMR(CDCl$_3$): 2.04-2.34(8H,m,—CH$_2$—), 2.40(6H, s,—CH$_3$), 2.56,2.80,2.91 (6H,t,t,t,>N—CH$_2$—), 3.22(1H,m,

≧—CH—), 3.91,4.11 (2H,m,m, —CON—CH$_2$—), 5.96 (1H,t,≧—CH—O—), 6.98-7.99 (7H,m,Ar—H).

$^{13}$C-NMR 20.61, 21.40, 22.90, 23.79, 27.69(2C), 33.66, 34.27, 42.65, 48.73(2C), 50.74, 79.57, 99.70, 107.36, 114.35, 118.63, 125.84, 126.43, 127.21(2C), 129.23(2C), 141.90, 141.91, 143.75, 155.11, 157.00, 163.78, 165.58, 166.57.

Compound 3. 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-methoxy-benzoate The reaction conditions were substantively the same, except that 4-methylbenzoylchloride was replaced with 4-methoxybenzoylchloride to obtain 0.26 g 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-methoxybenzoate, mp. 96.1-98.0° C.

$^1$H-NMR(CDCl$_3$): 2.08-2.22(6H,m,—CH$_2$—), 2.28(3H, s,—CH$_3$), 2.39(2H,t,—CH$_2$—), 2.65,2.82,3.27(6H,t,t,t, >N—CH$_2$—), 3.14(1H,m,

≧—CH—), 3.83(3H,s,—OCH$_3$), 3.89, 4.10 (2H,m,m, —CON—CH$_2$—), 5.93(1H,t,≧—CH—O—), 6.91-8.10 (7H,m,Ar—H).

$^{13}$C-NMR: 20.61, 22.90, 23.79, 27.69(2C), 33.66, 34.27, 42.65, 48.73(2C), 50.74, 55.25, 79.57, 99.70, 107.36, 114.24 (2C), 114.35, 118.63, 121.80, 125.84, 130.82(2C), 141.91, 143.75, 155.11, 157.00, 162.50, 163.78, 165.58, 166.57,

Compound 4. 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-fluorobenzoate The reaction conditions were substantively the same, except that 4-methylbenzoylchloride was replaced with 4-fluorobenzoylchloride.

$^{1}$HNMR: δ 1.94-2.12(6H m-CH$_2$—), 2.19 (3H s CH$_3$), 2.20-2.30(4H t-NCH$_2$—), 2.48(2H t-CH$_2$—),2.54(2H t-CH$_2$N—), 2.58(1H m >CH—), 2.61-2.76(2H m-CH$_2$—), 3.43-3.55(2H t-CH$_2$N—), 5.85(1H t >CHOC(C=O)—), 6.61(1H m Ar—H), 7.17-8.03(6H m Ar—H).

$^{13}$C-NMR: 20.61, 22.90, 23.79, 27.69(2C), 33.66, 34.27, 42.65, 48.73(2C), 50.74, 79.57, 99.70, 107.36, 114.31, 115.86(2C), 118.63, 125.84, 126.36, 130.25(2C), 141.91, 143.75, 155.11, 157.00, 163.87, 164.88, 165.58, 166.57.

Melting point: 226.1-227.6° C. (hydrochloride).

EXAMPLE 2

Synthesis of Carbonyl Carboxylic Acid Esters (Formula (IV)) of the Compound [Formula (II)]

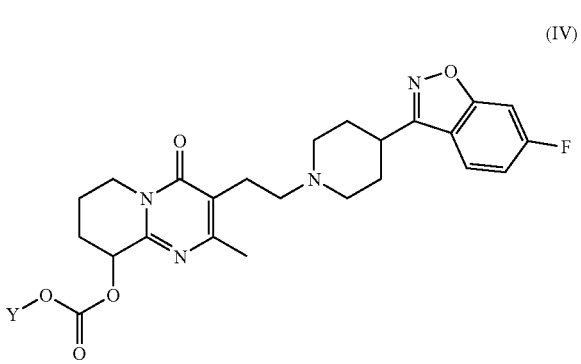

(IV)

A. General Methods and Processes

Reaction scheme:

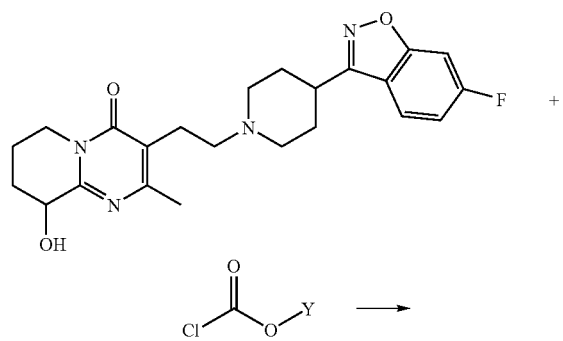

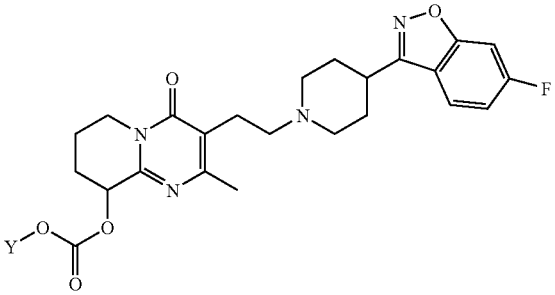

wherein Y is a saturated alkyl having 1-20 carbon atoms or an unsaturated alkyl having 2-20 carbon atoms or a cycloalkyl having 4-20 carbon atoms, such as methyl, ethyl, propyl, isopropyl, butyl, isobutyl, tert-butyl, pentyl and various isomers thereof, cyclohexyl, etc.; or an aryl having 7-20 carbon atoms, such as phenyl, tolyl, methoxyphenyl, etc.

Compound 5. 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl ethyl carbonate hydrochloride To 30 ml anhydrous dichloromethane and 3 ml anhydrous pyridine, 2.0 g (4.69 mmol) of the compound [formula (II)] was added, dissolved under stirring at room temperature, then 1.09 (9.38 mmol) ethyl chloroformate was added dropwise, and reacted until starting materials spots disappeared on TLC. The reaction was poured into a sufficient amount of water, adjusted to pH of 9 with 10% aqueous NaOH solution, and extracted with dichloromethane for three times (30 ml per time). The extract was washed with water, dried over anhydrous magnesium sulfate, and distilled at a reduced pressure to remove solvent. The residue was dissolved in 5 ml anhydrous ethanol, and then 5 ml of saturated anhydrous ethanol-HCl solution was added dropwise. After standing overnight, the precipitated solid was filtered out, washed with ethyl acetate, and dried to obtain 1.60 g of 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl ethyl carbonate hydrochloride, mp.: 229.0-229.5° C.

$^{1}$H-NMR(CDCl$_3$): 1.32(3H,t,—CH$_3$), 2.02-2.60(8H,m, —CH$_2$—), 2.39(3H,s,Ar—CH$_3$), 2.40-3.47(6H,m, >N—CH$_2$—), 3.22(1H, m, $$-\overset{O}{\underset{N}{\|}}-$$

≧—CH—), 3.91,4.11(2H,m,m,—CON—CH$_2$—), 4.23(2H, m,—OCH$_2$—), 5.96(1H,t,≧—CH—O—), 7.01-7.22(3H,m, Ar—H).

$^{13}$CNMR: 13.93, 20.61, 22.90, 24.02, 27.69(2C), 32.10, 34.27, 42.65, 48.73(2C), 50.74, 62.40, 81.82, 99.70, 107.36, 114.31, 118.63, 120.82, 126.83, 148.20, 150.05, 155.11, 163.78, 165.08, 166.57.

Compound 6. 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl isobutyl carbonate dihydrochloride To 30 ml anhydrous dichloromethane and 3 ml anhydrous pyridine, 2.0 g (4.69 mmol) of the compound [formula (II)]

was added, dissolved under stirring at room temperature, then 1.29 g (9.38 mmol) isobutyl chloroformate was added dropwise, and reacted until starting materials spots disappeared on TLC. The reaction was poured into a sufficient amount of water, adjusted to pH of 9 with 10% aqueous NaOH solution, and extracted with dichloromethane for three times (30 ml per time). The extracts were washed with water, dried over anhydrous magnesium sulfate, and distilled at a reduced pressure to remove solvent. The residue was dissolved in 5 ml anhydrous ethanol, and then 5 ml of saturated anhydrous ethanol-HCl solution was added dropwise. After standing overnight, the precipitated solid was filtered out, washed with ethyl acetate, and dried to obtain 1.65 g of 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl isobutyl carbonate dihydrochloride, mp.: 242.1-243.5° C.

$^1$H-NMR(DMSO-d$_6$): 0.88(6H,d,

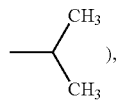

), 1.92-2.40(9H, m,—CH$_2$—,>CH—), 2.25(3H,s, Ar—CH$_3$), 2.99-3.12 (6H,m, >N—CH$_2$—), 3.50(1H,m,

≧—CH—), 3.70,3.97 (6H,m,m, —CON—CH$_2$—, —OCH$_2$—,Ar—CH$_2$—), 5.55(1H,t, ≧—CH—O—), 6.56 (1H,br,HCl), 7.31-8.18 (3H,m,Ar—H), 11.02(1H,br,HCl).

$^{13}$CNMR: 19.12(2C), 20.61, 22.90, 24.02, 27.83, 27.69 (2C), 32.10, 34.27, 42.65, 48.73(2C), 50.74, 70.66,81.82, 99.70, 107.36, 114.31, 118.63, 120.82, 126.83, 148.20, 150.05, 155.11, 163.78, 165.08, 166.57.

Compound 7. 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl n-pentyl carbonate dihydrochloride To 30 ml anhydrous dichloromethane and 3 ml anhydrous pyridine, 2.0 g (4.69 mmol) of the compound [formula (II)] was added, dissolved under stirring at room temperature, then 1.42 g (9.38 mmol) pentyl chloroformate was added dropwise, and reacted until starting materials spots disappeared on TLC. The reaction was poured into a sufficient amount of water, adjusted to pH of 9 with 10% aqueous NaOH solution, and extracted with dichloromethane for three times (30 ml per time). The extracts were washed with water, dried over anhydrous magnesium sulfate, and distilled at a reduced pressure to remove solvent. The residue was dissolved in 5 ml anhydrous ethanol, and then 5 ml of saturated anhydrous ethanol-HCl solution was added dropwise. After standing overnight, the precipitated solid was filtered out, washed with ethyl acetate, and dried to obtain 1.72 g of 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl n-pentyl carbonate dihydrochloride, mp.: 232.5-233.6° C.

$^1$H-NMR(DMSO-d$_6$): 0.86(3H,d,—CH$_3$), 1.30-1.61(8H, m,—CH$_2$—), 1.97-2.48(8H,m,—CH$_2$—), 2.32(3H,s, Ar—CH$_3$), 2.99-3.71 (6H,m, >N—CH$_2$—), 3.71(3H,m,

≧—CH—, Ar—CH$_2$—), 3.50,3.90 (6H,m,m,—CON—CH$_2$—),4.16 (2H,m,—OCH$_2$—),), 5.55(1H, t,≧—CH—O—),7.32-8.25(3H,m,Ar—H),8.46(1H,br, HCl),11.26 (1H, br, HCl).

$^{13}$CNMR:13.99, 20.61, 22.42, 22,90, 24.02, 27.69(2C), 28.23, 28.48, 32.10, 34.27, 42.65, 48.73(2C), 50.74, 64.64, 81.82, 99.70, 107.36, 114.31, 118.63, 120.82, 126.83, 148.20, 150.05, 155.11, 163.78, 165.08, 166.57.

Compound 8. 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl phenyl carbonate hydrochloride To 10 ml anhydrous dichloromethane and 1 ml anhydrous pyridine, 2.0 g (4.69 mmol) of the compound [formula (II)] was added, dissolved under stirring at room temperature, then 1.48 g (9.38 mmol) phenyl chloroformate was added dropwise, and reacted until starting materials spots disappeared on TLC. The reaction was extracted with dichloromethane for three times (15 ml per time). The extracts were washed with water, dried over anhydrous magnesium sulfate, and distilled at a reduced pressure to remove solvent. The residue was dissolved in 2 ml anhydrous ethanol, and then 3 ml of anhydrous ethanol-HCl saturated solution was added dropwise. After standing overnight, the precipitated solid was filtered out, washed with ethyl acetate, and dried to obtain 1.51 g of 3-{2-[4-(6-fluoro-1,2-benzoisoxazol-3-yl)-1-piperidinyl] ethyl}-2-methyl-4-oxo-6,7,8,9-tetrahydro-pyrido[1,2-α]pyrimidin-9-yl phenyl carbonate hydrochloride. Mp.: 186.7-187.8° C.

$^1$H-NMR(CDCl$_3$): 2.03-2.60(8H, m,—CH$_2$—), 2.43(3H, s,Ar—CH$_3$), 3.07,3.11(6H,m,>N—CH$_2$—), 3.46(1H, m,

≧—CH—),3.88, 3.98(2H,m,—CON—CH$_2$—), 5.65(1H,t, ≧—CH—O—), 6.78-7.40 (8H,m,Ar—H), 7.95 (1H,br, HCl).

$^{13}$CNMR: 20.61, 22.90, 24.02, 27.69(2C), 32.10, 34.27, 42.65, 48.73(2C), 50.74, 81.82, 99.70, 107.36, 114.31, 118.63, 120.82, 121.48(2C), 125.60, 127.92, 130.09(2C), 142.58, 150.05, 150.35, 155.11, 163.78, 165.08, 166.57.

Melting point: 249.2-251.5° C.

Compound 9. 3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl p-nitrophenyl carbonate hydrochloride To 10 ml anhydrous dichloromethane and 1 ml anhydrous pyridine, 2.0 g (4.69 mmol) of the compound [formula (II)] was added, dissolved under stirring at room temperature, then 1.91 g (9.38 mmol) p-nitrophenyl chloroformate was added dropwise, and reacted until starting materials spots disappeared on TLC. The reaction was extracted with dichloromethane for three times (15 ml per time). The extracts were washed with water, dried over anhydrous magnesium sulfate, and distilled at a reduced pressure to remove solvent. The residue was dissolved in 2 ml anhydrous ethanol, then 3 ml of anhydrous ethanol-HCl saturated solution was added dropwise. After standing overnight, the precipitated solid was filtered out, washed with ethyl acetate, and dried to obtain 1.69 g of 3-{2-[4-(6-fluoro-1,2-benzoisoxazol-3-yl)-1-piperidinyl]ethyl}-2-methyl-4-oxo-6,7,8,9-tetrahydro-pyrido [1,2-α]pyrimidin-9-yl p-nitrophenyl carbonate hydrochloride.

$^1$H-NMR(CDCl$_3$): 1.78-2.47(8H,m,—CH$_2$—), 2.35(3H,s, Ar—CH$_3$), 2.60,2.95,3.36 (6H,m,>N—CH$_2$—), 3.28(1H, m,

≧—CH—), 3.83(1H,s,HCl), 3.95,4.03 (2H,m, —CON— CH$_2$—), 5.58(1H,t,≧—CH—O—), 6.93-8.10(8H,m,Ar— H),7.95 (1H,br,HCl).

$^{13}$CNMR: 20.61, 22.90, 24.02, 27.69(2C), 32.10, 34.27, 42.65, 48.73(2C), 50.74, 81.82, 99.70, 107.36, 114.31, 118.63, 120.82, 122.18(2C), 125.18(2C), 127.92, 145.38, 148.20, 150.05, 155.11,155.47, 163.78, 165.08, 166.57.

EXAMPLE 3

Tests of the Compounds being Metabolized to Form the Active

Component, 3-{2-[4-(6-fluoro-1,2-benzoisoxazol-3-yl)-1-piperidinyl]ethyl}-9-hydroxy-2-methyl-6,7,8,9-tetrahydro-pyrido[1,2-α]pyrimidin-4-one, (the Compound [Formula (II)]) in Liver Cells 40 μg of the Compound 1 of Example 1 (or Compound 2 or Compound 3 or Compound 5 or Compound 6 or Compound 7 or Compound 8 or Compound 9) was dissolved in 0.01M potassium phosphate buffer solution (containing 1 mM NADPH), mixed with 25 μL of human liver cells S9 (20 mg protein/mL, H961), cultured at 37° C. for 2 hours, and then the mixture was quenched with concentrated perchloric acid. After the precipitated proteins were removed by centrifugation, the obtained supernatant solution was adjusted to pH of 3 with concentrated potassium phosphate solution, and centrifuged again. The obtained supernatant was directly injected into HPLC for analysis.

The metabolism results were shown in Table 1. The metabolic rates of the compounds being metabolized in liver cells for 2 hours to form the active component 3-{2-[4-(6-fluoro-1,2-benzoisoxazol-3-yl)-1-piperidinyl]ethyl}-9-hydroxy-2-methyl-6,7,8,9-tetrahydro-pyrido[1,2-α]pyrimidin-4-one (the compound [formula (II)]) ranged from 70% to 95%, depending on the different ester groups.

TABLE 1

Metabolic rates of the compounds in liver cells for 2 hours

| Compound | Metabolic rate (%) |
|---|---|
| Compound 1 | 89 |
| Compound 2 | 78 |
| Compound 3 | 87 |
| Compound 5 | 95 |
| Compound 6 | 92 |
| Compound 7 | 93 |
| Compound 8 | 94 |
| Compound 9 | 89 |

EXAMPLE 4

Measurement of the Absolute Bioavailability—Beagle Tests of the Compound [Formula (II)] and its Prodrugs, the Compounds 1, 2, 3, 5, 6, 7 and 8

Twenty one beagles weighing about 10 kg were divided into 7 groups, and intragastrically administered the compounds 1, 2, 3, 5, 6, 7 and 8 at a dosage of 9.4 μmol/beagle, respectively. Blood samples were taken at the predetermined time points, and the concentrations of the active metabolite (the compound [formula (II)]) and prodrugs in blood were measured. In the meantime, three beagles weighing about 10 kg were intravenously administered with the compound [formula (II)] at a dosage equimolar to the prodrug, as the control group, and the concentrations of the compound [formula (II)] in blood were measured.

Figure 1B:
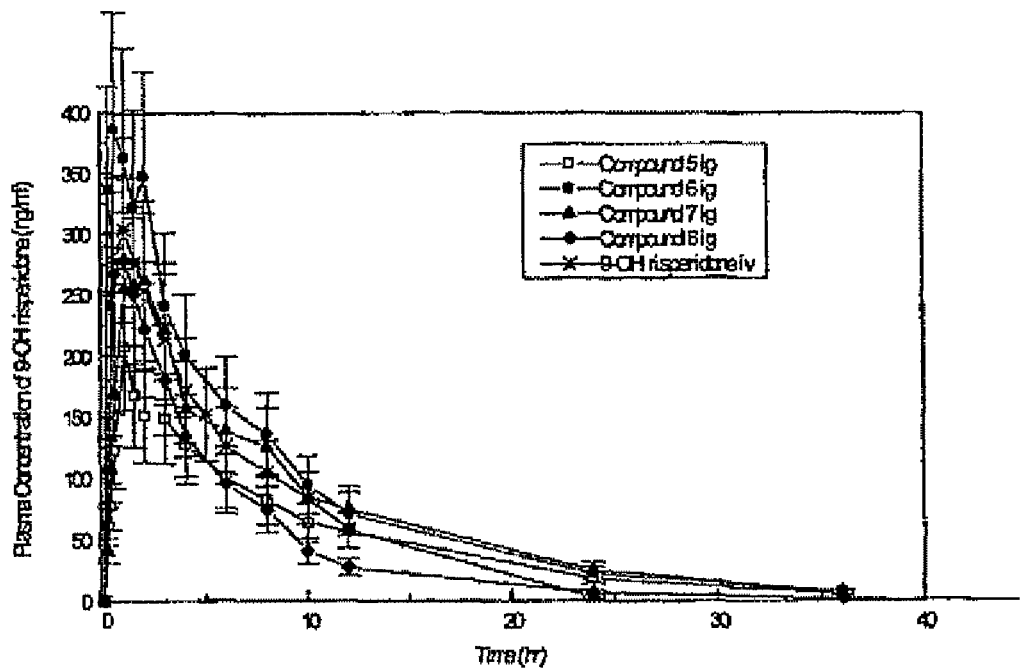
Figure 1C:
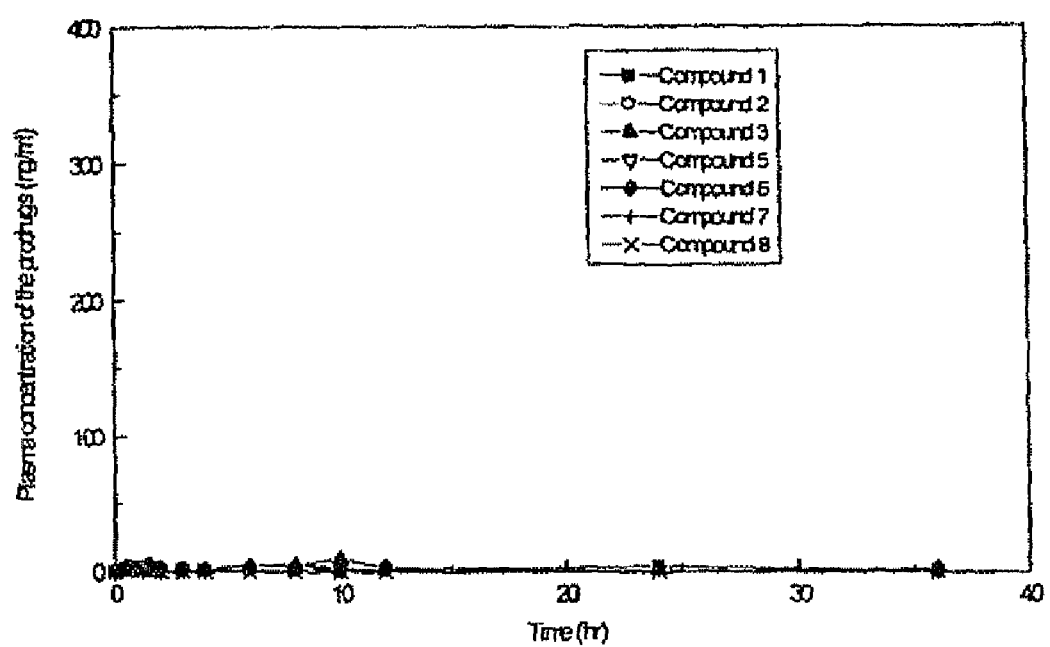

The results were shown in FIG. 1 and Table 2. The prodrugs were immediately metabolized almost completely to form the active metabolite in beagle body, the compound [formula (II)] upon being administrated parenterally, and the concentrations of the original compounds were very low (see: FIG. 1C). The results also indicated that the bioavailability of the prodrugs of the compound [formula (II)] were significantly higher than that of Invega (28%). Particularlly, the prodrugs of carbonate type had a very remarkable improvement of bioavailability.

TABLE 2

Comparison of test results of the prodrugs with those of the compound [formula (II)] in beagles - the concentrations of the active metabolite (the compound [formula (II)]) and those of the original compounds

| Administrating route | Compound | Cmax ng/ml | Tmax (hr) | T$_{1/2}$ (hr) | AUC (nghr/ml) | Absolute bioavailability (%) |
|---|---|---|---|---|---|---|
| i.g. | 1 | 223 | 1.5 | 6.08 | 1455 | 60.1 |
|  | 2 | 116 | 2.0 | 9.18 | 1283 | 53.0 |
|  | 3 | 90 | 1.5 | 11.6 | 1086 | 44.8 |
|  | 5 | 208 | 1.0 | 7.46 | 1854 | 76.5 |
|  | 6 | 386 | 0.5 | 7.09 | 2920 | 120.6 |
|  | 7 | 257 | 1.5 | 6.93 | 2561 | 105.7 |
|  | 8 | 279 | 1.0 | 7.14 | 1671 | 69.0 |
| iv | 9-hydroxy risperidone (the compound [formula (II)]) | 360 | — | 2.51 | 2422 | — |

EXAMPLE 6

Preparation of Oral Conventional Tablets

Ingredients:

| | |
|---|---|
| Compound 1 or Compound 6 or Compound 7 | 6% |
| Microcrystalline cellulose | 72% |
| Hydroxypropylmethyl cellulose | 8% |
| Calcium hydrogen phosphate dihydrate | 12% |
| Magnesium stearate | 0.8% |
| Colloid anhydrous silica | 1.2% |

Tablets were obtained by direct tabletting, and each tablet contained 6 mg of active ingredient (expressed in the compound [formula (II)]). The oral conventional tablets were subjected to dissolution tests, and the results were shown in table 3 below.

TABLE 3

Dissolution of the oral conventional tablets

| | | Dissolution time (hours) | | |
|---|---|---|---|---|
| | | 2 | 4 | 8 |
| Dissolution percentage of the active ingredient (%) | Compound 1 | 35 | 67 | 92 |
| | Compound 6 | 43 | 79 | 98 |
| | Compound 7 | 45 | 76 | 93 |

EXAMPLE 7

Preparation of Oral Sustained-Release Capsules

A. Granules:

| | |
|---|---|
| Compound 1 or Compound 6 or Compound 7 | 5% |
| Microcrystalline cellulose | 91% |
| Hydroxypropylmethyl cellulose | 4% |

Granules were obtained by using conventional fluidized bed.

B. Coating:

| | |
|---|---|
| Ethyl cellulose | 85% |
| Hydroxypropylmethyl cellulose | 15% |

After the coating was dried, the coated granules were filled into hard gelatin capsules, each capsule contain 6 mg of the active ingredient (expressed in the compound [formula (II)]), and the coating degree was 6%. The capsules were subjected to dissolution tests according the method specified in the Pharmacopoeia of the People's Republic of China. The results were shown in table 4 below.

TABLE 4

Dissolution of oral sustained-release capsules of Compound 1

| | | Dissolution time (hours) | | | | |
|---|---|---|---|---|---|---|
| | | 2 | 4 | 8 | 12 | 24 |
| Dissolution percentage of the active ingredient (%) | Compound 1 | 8.9 | 26 | 60 | 76 | 94 |
| | Compound 6 | 8.8 | 19 | 42 | 68 | 89 |
| | Compound 7 | 5.3 | 22 | 41 | 59 | 82 |

What is claimed is:

1. A compound of formula (I),

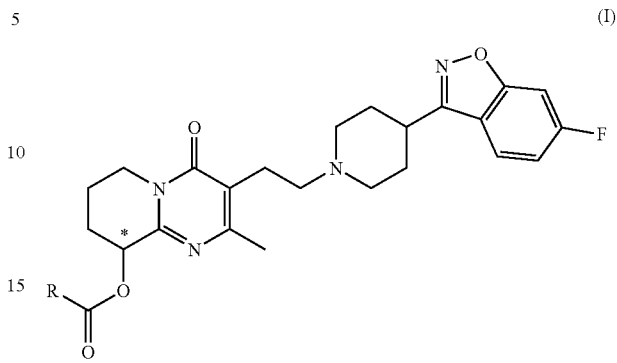

wherein,
the chiral center (*) can be R or S or RS (racemic mixture);
R is an aryl having 7-20 carbon atoms; or a saturated alkoxy having 1-20 carbon atoms or an unsaturated alkoxy having 2-20 carbon atoms or a cycloalkoxy having 4-20 carbon atoms or an arylalkoxy having 7-20 carbon atoms; or
an optical isomer thereof or a pharmaceutically salt thereof.

2. The compound according to claim 1, wherein,
R is an aryl having 7-20 carbon atoms.

3. The compound according to claim 1, wherein,
R is a saturated alkoxy having 1-20 carbon atoms or an unsaturated alkoxy having 2-20 carbon atoms or a cycloalkoxy having 4-20 carbon atoms.

4. The compound according to claim 1 comprising a salt of the compound of formula (I), wherein the salt of the compound is one of hydrochloride, sulfate, maleate, succinate, and other salts formed with a pharmaceutically acceptable acid.

5. The compound according to claim 1, wherein the compound is selected from the group consisting of:
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl benzoate,
3-{2-[4-(6-fluoro-1,2-benzoisoxazol-3-yl)-1-piperidinyl]ethyl}-2-methyl-4-oxo-6,7,8,9tetrahydro-pyrido[1,2-α]pyrimidin-9-yl 2-methylbenzoate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]-yl 3-methylbenzoate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-methylbenzoate,
3-{2-[4-(6-fluoro-1,2-benzoisoxazol-3-yl)-1-piperidinyl]ethyl }-2-methyl-4-oxo-6,7,8,9-tetrahydro-pyrido[1,2-α]pyrimidin-9-yl 2-methoxybenzoate,
3-{2-[4-(6-fluoro-1,2-benzoisoxazol-3-yl)-1-piperidinyl]ethyl}-2-methyl-4-oxo-6,7, 8,9-tetrahydro-pyrido[1,2-α]pyrimidin-9-yl 3-methoxybenzoate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-methoxybenzoate,
3-{2-[4-(6-fluoro-1,2-benzoisoxazol-3-yl)-1-piperidinyl]ethyl}1-2-methyl-4-oxo-6,7,8,9-tetrahydro-pyrido[1,2-α]pyrimidin-9-yl 2-fluorobenzoate, 3-{2-[4-(6-fluoro-1,2-benzoisoxazol-3-yl)-1-piperidinyl]ethyl}1-2-methyl-4-oxo-6,7,8,9-tetrahydro-pyrido[1,2-α]pyrimidin-9-yl 3-fluorobenzoate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-fluorobenzoate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-carboxybenzoate,
3-{2-[4-(6-fluoro-1,2-benzoisoxazol-3-yl)-1-piperidinyl]ethyl}1-2-methyl-4-oxo-6,7,8,9-tetrahydro-pyrido[1,2-α]pyrimidin-9-yl methyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl ethyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl propyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl isopropyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl butyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl isobutyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl tert-butyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-methylbutyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl n-pentyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-pentyl carbonate,
3-{2-[4-(6-fluoro-1,2-benzoisoxazol-3-yl)-1-piperidinyl]ethyl}1-2-methyl-4-oxo-6,7,8,9-tetrahydro-pyrido[1,2-α]pyrimidin-9-yl 3-pentyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl isopentyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl neopentyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl hexyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl cyclohexyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl phenyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-methylphenyl carbonate,
3-{2-[4-(6-fluoro-1,2-benzoisoxazol-3-yl)-1-piperidinyl]ethyl}-2-methyl-4-oxo-6,7, 8,9-tetrahydro-pyrido[1,2-α]pyrimidin-9-yl 3-methylphenyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-methylphenyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-methoxyphenyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 3-methoxyphenyl carbonate,
3-{2-[4-(6-fluoro-1,2-benzoisoxazol-3-yl)-1-piperidinyl]ethyl}1-2-methyl-4-oxo-6,7,8,9-tetrahydro-pyrido[1,2-α]pyrimidin-9-yl 4-methoxyphenyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 2-fluorophenyl carbonate,
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 3-fluorophenyl carbonate, and
3-{2-[4-(6-fluoro-1,2-benzoisoxazol-3-yl)-1-piperidinyl]ethyl}-2-methyl-4-oxo-6,7,8,9-tetrahydro-pyrido[1,2-α]pyrimidin-9-yl 4-fluorophenyl carbonate, and
various salts and optical isomers thereof.

6. A pharmaceutical composition comprising a compound according to claim 1, and a pharmaceutically acceptable carrier.

7. A method of treating a mental disorder, comprising administering to a patient a compound according to claim 1.

8. The pharmaceutical composition according to claim 6, wherein the composition is administrated by oral, injection, transdermal, intranasal, or mucosal mode or by inhalation administration.

9. The pharmaceutical composition according to claim 8, wherein the composition is presented in conventional, sustained-release, controlled-release, site specific delivery or fast release dosage form.

10. The compound according to claim 1, wherein R is

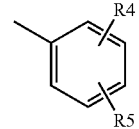

wherein, R4 and R5 independently are hydrogen, a saturated alkyl having 1-6 carbon atoms or alkoxy having 1-6 carbon atoms, an unsaturated alkyl having 2-6 carbon atoms, OH, Cl, F, CN, carboxyl or ester group.

11. The compound according to claim 10, wherein R4 and R5 independently are hydrogen, methyl, ethyl, methoxy, ethoxy, fluorine or carboxyl.

12. The compound according to claim 1, wherein R is a saturated alkoxy having 1-10 carbon atoms or an unsaturated alkoxy having 2-10 carbon atoms or a cycloalkoxy having 4-10 carbon atoms; or an arylalkoxy having 7-20 carbon atoms.

13. The compound according to claim 1, wherein R is

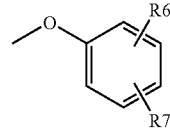

wherein
R6 and R7 independently are hydrogen, a saturated alkyl having 1-6 carbon atoms or alkoxy having 1-6 carbon atoms, an unsaturated alkyl having 2-6 carbon atoms, OH, Cl, F, CN, carboxyl or ester group.

14. The compound according to claim 13, wherein R6 and R7 independently are hydrogen, methyl, ethyl, methoxy, ethoxy, fluorine or carboxyl.

15. The pharmaceutical composition according to claim 9, wherein the composition is presented in an oral sustained-release dosage form, sustained-release microspheres, or implants.

16. The method according to claim 7, wherein the mental disorder is schizophrenia.

* * * * *

UNITED STATES PATENT AND TRADEMARK OFFICE
CERTIFICATE OF CORRECTION

PATENT NO. : 8,314,110 B2
APPLICATION NO. : 12/596516
DATED : November 20, 2012
INVENTOR(S) : Youxin Li It is certified that error appears in the above-identified patent and that said Letters Patent is hereby corrected as shown below:

Column 18, Line 47, Claim 5, delete "9tetrahydro" and insert -- 9-tetrahydro --

Column 18, Line 51, Claim 5, delete "α]-yl" and insert -- α]-pyrimidin-9-yl --

Column 18, Line 57, Claim 5, delete "ethyl }" and insert -- ethyl} --

Column 18, Line 60, Claim 5, delete "6,7, 8,9" and insert -- 6,7,8,9 --

Column 18, Line 66, Claim 5, delete "ethyl}1-2" and insert -- ethyl}-2 --

Column 19, Line 2, Claim 5, delete "ethyl}1-2" and insert -- ethyl}-2 --

Column 19, Line 11, Claim 5, delete "ethyl}1-2" and insert -- ethyl}-2 --

Column 19, Line 16, Claim 5, delete "fluoro-1 ,2" and insert -- fluoro-1,2 --

Column 19, Line 25, Claim 5, delete "fluoro-1 ,2" and insert -- fluoro-1,2 --

Column 19, Line 40, Claim 5, delete "ethyl}1-2" and insert -- ethyl}-2 --

Column 19, Line 60, Claim 5, delete "6,7, 8,9" and insert -- 6,7,8,9 --

Column 20, Line 5, Claim 5, delete "ethyl}1-2" and insert -- ethyl}-2 --

Signed and Sealed this
Nineteenth Day of February, 2013

Teresa Stanek Rea
*Acting Director of the United States Patent and Trademark Office*